United States Patent
Wong et al.

(10) Patent No.: US 9,855,723 B2
(45) Date of Patent: Jan. 2, 2018

(54) DISSIMILAR MATERIAL AFFIXMENT APPARATUS, COMPOSITION, AND METHOD

(71) Applicants: Alan Wong, Federal Heights, CO (US); Howard Steven Rosen, Denver, CO (US)

(72) Inventors: Alan Wong, Federal Heights, CO (US); Howard Steven Rosen, Denver, CO (US)

(*) Notice: Subject to any disclaimer, the term of this patent is extended or adjusted under 35 U.S.C. 154(b) by 583 days.

(21) Appl. No.: 14/567,620

(22) Filed: Dec. 11, 2014

(65) Prior Publication Data
US 2015/0099097 A1    Apr. 9, 2015

Related U.S. Application Data

(63) Continuation-in-part of application No. 13/751,033, filed on Jan. 25, 2013, now Pat. No. 8,939,766, which
(Continued)

(51) Int. Cl.
| | |
|---|---|
| *B32B 7/12* | (2006.01) |
| *A61C 13/15* | (2006.01) |
| *A61C 3/08* | (2006.01) |
| *B32B 15/08* | (2006.01) |
| *B32B 15/18* | (2006.01) |
| *B32B 18/00* | (2006.01) |

(Continued)

(52) U.S. Cl.
CPC ............... *B32B 7/12* (2013.01); *A61C 3/08* (2013.01); *A61C 19/004* (2013.01); *B32B 15/08* (2013.01); *B32B 15/18* (2013.01); *B32B 18/00* (2013.01); *B32B 37/1284* (2013.01); *B32B 37/142* (2013.01); *B32B 37/18* (2013.01); *B32B 38/0008* (2013.01); *B32B 38/0012* (2013.01); *B32B 38/162* (2013.01); *B32B 2038/0016* (2013.01); *B32B 2307/746* (2013.01); *B32B 2311/30* (2013.01); *B32B 2315/02* (2013.01); *G02B 6/3624* (2013.01); *Y10T 428/24752* (2015.01)

(58) Field of Classification Search
CPC ....... A61C 19/004; B32B 18/00; B32B 15/08; B32B 15/18; B32B 37/1284; B32B 37/142; B32B 37/18; B32B 38/0008; B32B 38/0012; B32B 38/162
USPC ................... 156/293, 153, 275.7, 275.5
See application file for complete search history.

(56) References Cited

U.S. PATENT DOCUMENTS

| | | | |
|---|---|---|---|
| 4,325,647 A * | 4/1982 | Maier .............. | C04B 37/005 403/179 |
| 4,356,047 A | 10/1982 | Gordon et al. | |

(Continued)

*Primary Examiner* — Daniel Wiley
(74) *Attorney, Agent, or Firm* — Roger A. Jackson

(57) ABSTRACT

An apparatus, composition, and method for affixment of dissimilar materials, that includes a ceramic longwise member having a distal portion and a proximal portion that has a pilot, also included is a steel receptacle including primary and secondary voids that are co-axial and in communication with one another. The longwise member pilot is received in the primary void with the remainder of the proximal portion having an open gap within the secondary void, wherein adhesive is disposed within the open gap and the distal portion projects beyond the receptacle. Operationally, resulting in the longwise member and the receptacle resisting a separating force apart from one another.

10 Claims, 10 Drawing Sheets

Related U.S. Application Data is a continuation-in-part of application No. 13/293,948, filed on Nov. 10, 2011, now abandoned, which is a continuation-in-part of application No. 13/086,057, filed on Apr. 13, 2011, now abandoned, which is a continuation-in-part of application No. 12/763,159, filed on Apr. 19, 2010, now abandoned.

(51) Int. Cl.

| | | |
|---|---|---|
| *B32B 37/12* | (2006.01) | |
| *B32B 37/14* | (2006.01) | |
| *B32B 37/18* | (2006.01) | |
| *B32B 38/00* | (2006.01) | |
| *B32B 38/16* | (2006.01) | |
| *G02B 6/36* | (2006.01) | |

(56) References Cited

U.S. PATENT DOCUMENTS

| | | | |
|---|---|---|---|
| 4,457,972 A | | 7/1984 | Griffith et al. |
| 4,575,047 A | * | 3/1986 | Boos .................. F16B 11/006 |
| | | | 137/468 |
| 4,723,863 A | * | 2/1988 | Takagi .................. B23K 1/18 |
| | | | 228/132 |
| 4,784,574 A | * | 11/1988 | Tsuno .................. F01D 5/025 |
| | | | 403/30 |
| 4,939,101 A | | 7/1990 | Black et al. |
| 5,096,769 A | * | 3/1992 | Morgan .............. C04B 37/028 |
| | | | 174/152 GM |
| 9,157,483 B2 | * | 10/2015 | Buurlage .............. F16D 1/068 |
| 9,429,244 B2 | * | 8/2016 | Gao ...................... F16K 1/38 |

\* cited by examiner

DISSIMILAR MATERIAL AFFIXMENT APPARATUS, COMPOSITION, AND METHOD

RELATED APPLICATIONS

This is a continuation in part (CIP) patent application of U.S. patent application Ser. No. 13/751,033 filed on Jan. 25, 2013 by Alan Wong et al. of Federal Heights, Colo., US, that is a continuation in part (CIP) patent application of U.S. patent application Ser. No. 13/293,948 filed on Nov. 10, 2011 by Alan Wong et al. of Federal Heights, Colo., US, that is a continuation in part (CIP) patent application of U.S. patent application Ser. No. 13/086,057 filed on Apr. 13, 2011 by Alan Wong et al. of Federal Heights, Colo., US, that is a continuation in part (CIP) patent application of U.S. patent application Ser. No. 12/763,159 filed on Apr. 19, 2010 by Alan Wong of Federal Heights, Colo., US.

TECHNICAL FIELD

The present invention generally relates to a joining or affixing of dissimilar materials. More particularly, the present invention is an attempted solution to a problem of affixing materials that are dissimilar in composition and therefore are dissimilar in material properties; such as molecular structure, thermal expansion/thermal contraction characteristics, modulus of elasticity, compressive/tensile failure stresses, corrosion, galvanic, energy retention, energy transfer, hardness, creep, ductility, fracture resistance, plasticity (permanent strain versus reversible strain), poisons ratio (lateral to axial strain ratio), shear modulus to tensile modulus, specific heat capacity, thermal properties related to heat gain/loss for property changes, heat transfer, all of the above as a sampling of numerous dissimilar material properties to consider when dissimilar materials are affixed to one another.

BACKGROUND OF INVENTION

The need for joining or affixing dissimilar materials is in widespread existence, as the difference in properties of the materials are needed, such as a glass window for transparency affixed to a metal frame for support and strength, or a corrosion resistant material such as copper that is soft being affixed to a steel structure for strength, or a paint affixed to a resilient material such as a car bumper, or a chrome plating on a plastic material for appearance, or weight savings, or cost savings, and the like. Thus the want or need for affixing dissimilar materials outweighs the problems that affixing dissimilar materials causes. Thus this whole need or desire to join dissimilar materials stems from generally wanting to tailor engineer properties, for instance a particular part needing a high or low temperature resistance in a particular area (i.e. a temperature probe), or corrosion resistance in a certain area (i.e. a boat hull), abrasion or wear resistance in a certain area (i.e. a gear), or in electronics affixing of a non-conductive material to a conductive material (i.e. semiconductor chips, batteries), as just a few examples.

The range of dissimilarity is key to understand in solving the problem of affixing materials, such that slightly dissimilar materials would be basically alike materials with minor differences, such as two different types of steels or a variation within a material category such as affixing two different types of aluminum together. Next on the dissimilarity scale would be dissimilar materials such as steel to copper. For the highest level of dissimilarity of affixing materials would be two completely different material compositions, such as a ceramic material to metal or an organic material to metal. Thus the highly dissimilar material affixing presents the highest challenge as the interface of the highly dissimilar materials are subject to dramatic reactive differences in the two materials to various environmental conditions. As an example, for a ceramic material to a metal, wherein when these two materials are exposed to an environmental temperature change, the steel will move greatly relative to the ceramic causing this relative movement to have to be accommodated in whatever structure is used for the affixment, i.e. rivets, bolts, adhesives, interference fits, threads, welding, and the like, or else failure of the affixment will occur.

For the highest material dissimilarity situation, for instance steel to ceramic, the options are more limited, as certainly welding is not an option due to great dissimilarity in material melting temperatures, i.e. such that welding really requires that the materials be in the slightly dissimilar category, then looking at mechanical fastening could be a possibility (bolts, threads, rivets, etc.), however, the holes that the mechanical fastening requires can have added problems of causing stress points, also selected the material of the fasteners themselves can be challenging, plus due to the size and configuration of the parts to be affixed to one another, mechanical fastening may not be a good option. This leaves adhesives that can overcome the problems of welding and mechanical fasteners, however, causing a few of their own issues, such as bonding of the adhesive to the material, and material properties of the adhesive itself for temperature, corrosion, shear and tensile strength.

However, the wide ease of application (relative to welding and mechanical fastening) and the ability to accommodate the most difficult of highly dissimilar material affixing makes adhesives attractive to use, plus there are ever expanding options for different types of adhesives, also adhesives have a small weight component (relative to welding and mechanical fastening) and can distribute loading as between the materials in a more distributed manner again (relative to welding and mechanical fastening). Drawbacks of adhesives are the permanent affixment, thus making disassembly only available via causing material damage (much the same as welding), also environmental conditions, such as temperature, corrosives, aging, and the like can operate to change the bonding characteristics of the adhesive leading to dissimilar material separation-sometimes this can happen rather suddenly as opposed to a gradual dissimilar material separation, which would normally be preferred in a failure mode, in addition an adhesive requirement of meticulous surface preparation of the dissimilar materials to be affixed can be critical in the adhesive bonding property. Thus adhesives while favored are not perfect for affixing dissimilar materials due to the above mentioned issues with adhesives in affixing dissimilar materials.

Looking at the prior art related to dissimilar material affixing, particularly concerning semiconductor chips, in U.S. Pat. No. 4,356,047 to Gordon et al., disclosed is a ceramic lid assembly that includes an integral heat fusible layer defining a hermetic sealing area provided around the periphery of a ceramic lid for hermetic sealing of semiconductor chips in a flat pack that acts to protect the chip internal components. In Gordon, the integral heat fusible layer includes a metallized layer, an oxidation inhibiting layer, and a pre-flowed solderable layer in registration with each other in the hermetic sealing area, wherein the lid is of substantially non-conductive or dielectric material having a thickness range of from 0.010-0.040 inch. As stated in Gordon, ceramic material is generally preferred as it is inexpensive, easily metallized and has a coefficient of thermal expansion which matches that of the semiconductor flat pack, thus ceramic material found suitable includes the oxides of aluminum, beryllium, and magnesium. Gordon had discovered that single crystal sapphire is ideally suited for use as a lid in hermetic sealing of EPROMs by being transparent to ultra-violet light and the use of single crystal sapphire provides a large window opening for easy accessibility to the semiconductor chip for erasing and programming the Read Only Memory, see; abstract, column 3, lines 39-56. Thus, in Gordon, the affixment of the ceramic in the form of sapphire to bond at the outer periphery via a wettable metal layer with a metallized layer to heat fuse the ceramic lid to the flat pack for a hermetic seal is utilized.

Continuing in the prior art related to dissimilar material affixing, particularly in affixing an insulator surface with a conductive surface, in U.S. Pat. No. 4,457,972 to Griffith et al., disclosed is an enhanced adhesion by high energy bombardment. Wherein Griffith has films of gold, copper, silicon nitride, or other materials that are firmly bonded to insulator substrates such as silica, a ferrite, or Teflon (polytetrafluoroethylene) by irradiating the interface with high energy ions. Apparently, according to Griffith, track forming processes in the electronic stopping region cause intermixing in a thin surface layer resulting in improved adhesion without excessive doping (meaning surface material property changes), thus the high energy facilitates thick layers that can be bonded by depositing or doping the interfacial surfaces with fissionable elements or alpha emitters. Griffith states that the substrates were commercial grade Teflon, sapphire, nickel-zinc ferrite, fused quartz and soda-lime glass, with the substrates being cleaned with trichloroethylene, nitric acid and methanol before being loaded into a diffusion-pumped evaporator, wherein 200 to 500 Angstrom thick films of gold or copper were evaporated onto the substrates in a vacuum of 1 times 10 to the negative sixth power Torr., wherein silicon tetra nitrogen films on silicon were formed by sputter deposition in an RF discharge sputtering chamber. According to Griffith, after irradiation the adhesion of the films, they were tested by means of the "Scotch Tape Test": wherein a piece of tape was firmly pressed on the irradiated surface and slowly peeled off by hand, with the adhesion effect obtained after the high energy bombardment is so dramatic that more quantitative tests of adhesion were not necessary. Griffith primarily is applied to enhanced bonding with Aluminum on Teflon; see abstract, column 5, lines 22-38.

Further looking at the prior art related to dissimilar material affixing, again particularly concerning semiconductor chips, in U.S. Pat. No. 4,939,101 to Black, et al., disclosed are foregoing objects that are accomplished by cleaning the wafer surfaces to be bonded, being in particular silicon on sapphire, placing the wafer surfaces to be bonded in contact, annealing the bonded wafers at an elevated temperature to seal the interface and then further annealing the wafers at an elevated temperature in the presence of a hydrostatic pressure in excess of 300 psi. Black has in one embodiment; the hydrostatic pressure being up to about 15,000 psi, wherein the high temperature/high pressure annealing eliminates voids at the bonded interface thereby leaving a void free bonded interface. According to Black the benefit of semiconductor-on-insulator (SOI) devices are because the high isolation provided between adjacent devices by the insulating substrate.

What is needed is a structure and method of affixing a ceramic to a steel that does not require excessive heat or pressure nor a convoluted surface configuration of the ceramic that could add stress risers to the ceramic piece wherein the ceramic piece and the steel piece are each cylindrical in shape utilizing an adhesive as a bonding material as between the ceramic and the steel, wherein a primary separating force between the ceramic and the steel would be in shear, thus placing the adhesive in shear, wherein further requirements would be that the adhesive is of a medical grade and is capable of withstanding multiple cycles of heat sterilization.

SUMMARY OF INVENTION

The present invention provides an apparatus and composition for affixment of dissimilar materials, wherein the apparatus and composition include a ceramic longwise member having a proximal end portion and an opposing distal end portion with a longwise axis spanning therebetween. The proximal end portion further having a pilot portion and a suspended portion, with the longwise member having an outer surface. Also included in the apparatus and composition is a steel receptacle including a first end portion and an opposing second end portion with a longitudinal axis spanning therebetween. The first end portion having a primary void that is about the longitudinal axis and the second end portion having a secondary void that is about the longitudinal axis, wherein the primary and secondary voids are co-axial to one another, plus further the primary and secondary voids are in communication with one another.

The primary void defining a primary interior and the secondary void defining a secondary interior, with the secondary void terminating in an aperture that is oppositely positioned from the primary void, wherein the longwise member proximal end portion is received within the primary and secondary voids wherein the longwise axis and the longitudinal axis are co-axial. Also the primary void has a slidable contacting interface with the pilot portion of the longwise member outer surface, wherein the primary interior is consumed by the pilot portion of the longwise member, and the secondary void forms an open gap volume about the suspended portion of the longwise member outer surface. Wherein the secondary interior is further defined by the open gap volume plus the suspended portion of the longwise member, wherein the distal end portion of the longwise member projects beyond the aperture in a cantilever configuration.

Further included in the apparatus is the composition of an adhesive disposed within the open gap volume that is operational to affix the secondary void to the suspended portion of the longwise member outer surface resulting in the longwise member and the receptacle resisting a separating force along the longwise and the longitudinal axes.

These and other objects of the present invention will become more readily appreciated and understood from a consideration of the following detailed description of the exemplary embodiment(s) of the present invention when taken together with the accompanying drawings, in which;

REFERENCE NUMBERS IN DRAWINGS

Figure 1:
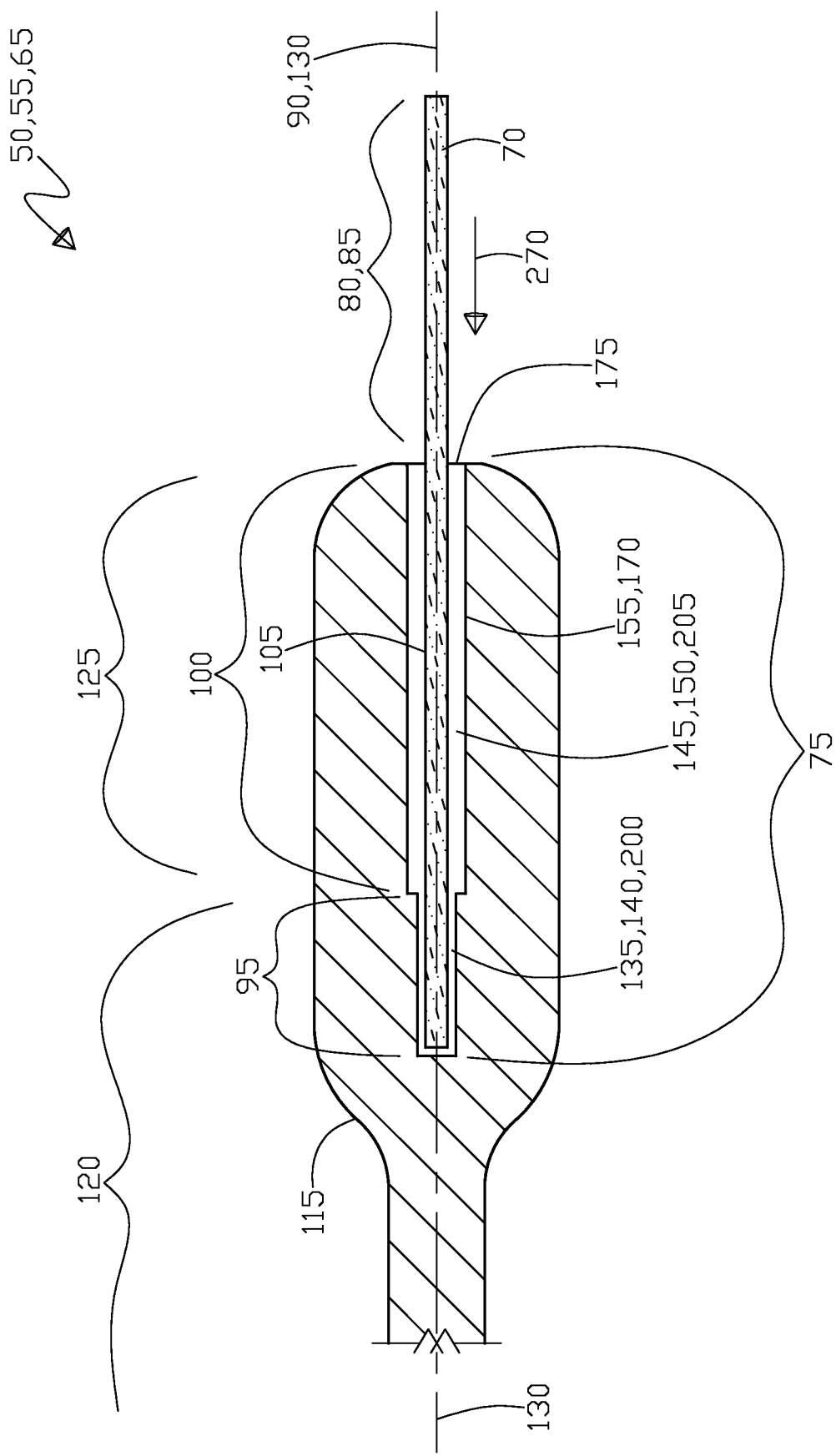
FIG. 1 is a cross sectional view of the receptacle and ceramic longwise member wherein the pilot portion of the longwise member is inserted into a primary void of the receptacle having a slidable contacting interface, further shown is a retention gap and a cantilever configuration of a distal end portion of the longwise member.

50 Dissimilar material affixment apparatus, composition, and method
55 Apparatus
60 Composition
65 Method
70 Ceramic longwise member
75 Proximal end portion of the ceramic longwise member 70
80 Distal end portion of the ceramic longwise member 70
85 Cantilever configuration of the distal end portion 80
90 Longwise axis of the ceramic longwise member 70
95 Pilot portion of the ceramic longwise member 70
100 Suspended portion of the ceramic longwise member 70
105 Outer surface of the ceramic longwise member 70
110 Ground outer surface of the proximal end portion 75
115 Steel receptacle
120 First end portion of the steel receptacle 115
125 Second end portion of the steel receptacle 115
130 Longitudinal axis of the steel receptacle 115
135 Primary void of the steel receptacle 115
140 Primary interior of the primary void 135
145 Secondary void of the steel receptacle 115
150 Secondary interior of the secondary void 145
155 Inner secondary surface of the secondary interior 150
160 Female right hand thread helix groove of the inner secondary surface 155
165 Female left hand thread helix groove of the inner secondary surface 155
170 Finish of the inner secondary surface 155 to about 150-250 RMS
175 Aperture of the secondary void 145
180 Tertiary void
185 Tertiary interior of the tertiary void 180
190 Retention gap volume of the tertiary interior 185
195 Greater distance extension of the tertiary interior 185 from the longitudinal axis 130 then the aperture 175 distance from the longitudinal axis 130
200 Slidable contacting interface as between the primary void 135 and the pilot portion 95
205 Open gap volume of the secondary void 145 that is about the suspended portion 100
210 Adhesive
215 Separating axial force as between the longwise member 70 and the receptacle 115 along the longwise 90 and longitudinal 130 axes
220 Rotational force about the longwise 90 and longitudinal 130 axes
225 Soap for cleaning
230 Hot water for cleaning
235 Brush for cleaning
240 Ultrasonic alkaline bath for cleaning
245 Ultrasonic acidic bath for cleaning
250 De-ionized water for cleaning
255 Flushing with alcohol for cleaning
260 Flushing with acetone for cleaning
265 Passivating with heat for cleaning and corrosion protection
270 Inserting the longwise member 70 into the receptacle 115 such that the proximal end portion 75 is inserted into the primary interior 140
275 Ultraviolet light
280 Curing the adhesive with ultraviolet light 275

DETAILED DESCRIPTION

Figure 2:
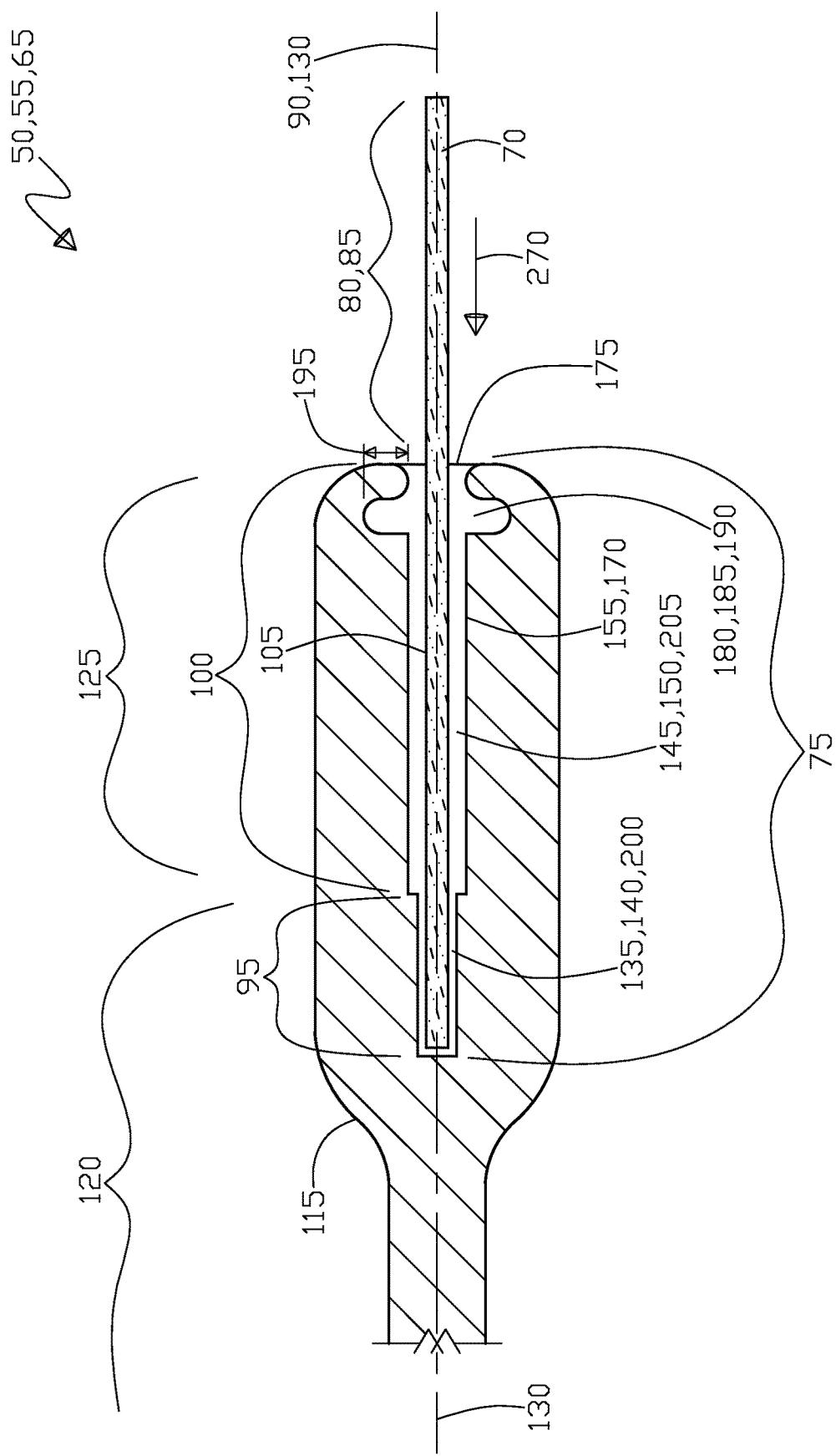
FIG. 2 is a cross sectional view of the receptacle and ceramic longwise member wherein the pilot portion of the longwise member is inserted into the primary void of the receptacle having the slidable contacting interface, further shown is the retention gap, and a tertiary void with the cantilever configuration of the distal end portion of the longwise member.

Starting with FIG. 1, is cross sectional view of the receptacle 115 and ceramic longwise member 70 wherein the pilot portion 95 of the longwise member 70 is inserted into a primary void 135 of the receptacle 115 having a slidable contacting interface 200, further shown is a retention gap 190, and a cantilever configuration 85 of a distal end portion 80 of the longwise member 70. Next, FIG. 2 is a cross sectional view of the receptacle 115 and ceramic longwise member 70 wherein the pilot portion 95 of the longwise member 70 is inserted into the primary void 135 of the receptacle 115 having the slidable contacting interface 200, further shown is the retention gap 190, and a tertiary void 180 with the cantilever configuration 85 of the distal end portion 80 of the longwise member 70.

Figure 3:
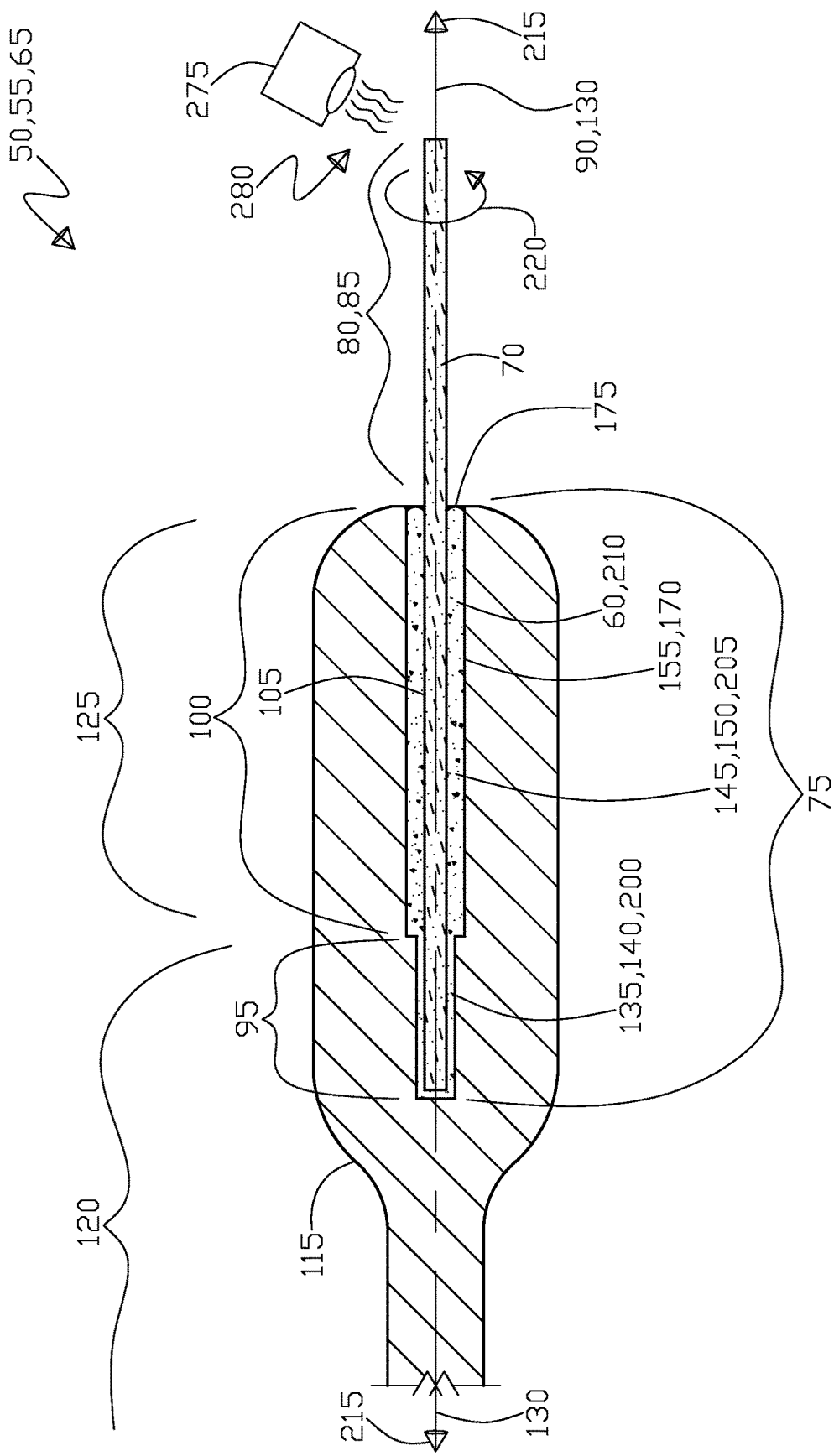
FIG. 3 is a cross sectional view of the receptacle and ceramic longwise member wherein the pilot portion of the longwise member is inserted into the primary void of the receptacle having the slidable contacting interface, further shown is the retention gap and the cantilever configuration of the distal end portion of the longwise member, along with an adhesive that is disposed within the open gap volume.
Figure 4:
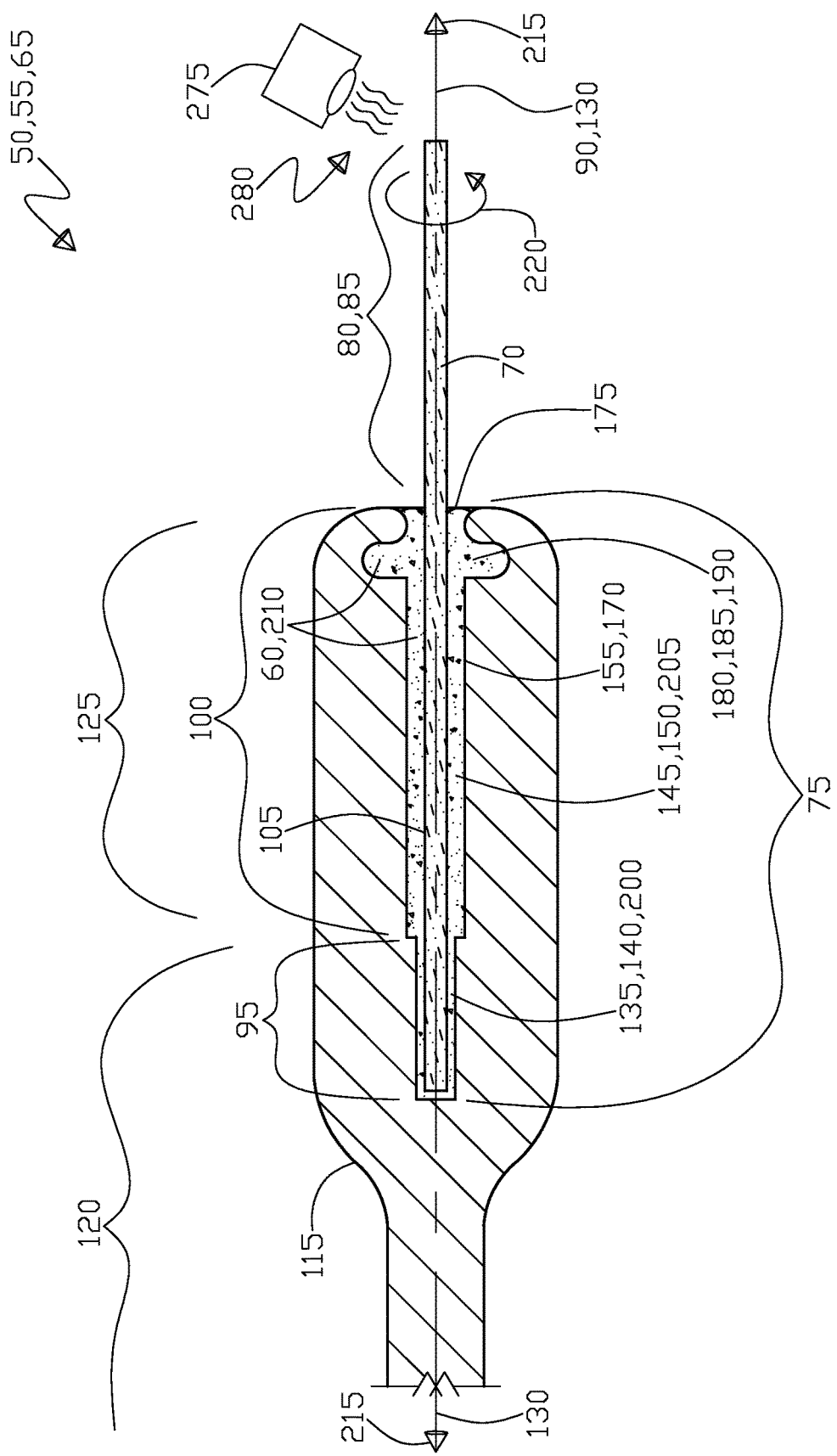
FIG. 4 is a cross sectional view of the receptacle and ceramic longwise member wherein the pilot portion of the longwise member is inserted into the primary void of the receptacle having the slidable contacting interface, further shown is the retention gap, and the tertiary void with the cantilever configuration of the distal end portion of the longwise member, along with an adhesive that is disposed within the open gap volume and the tertiary void.

Continuing, FIG. 3 is a cross sectional view of the receptacle 115 and ceramic longwise member 70 wherein the pilot portion 95 of the longwise member 70 is inserted 270 into the primary void 135 of the receptacle 115 having the slidable contacting interface 200, further shown is the retention gap 190 and the cantilever 85 configuration of the distal end portion 80 of the longwise member 70, along with an adhesive 210 that is disposed within the open gap volume 205. Next, FIG. 4 is a cross sectional view of the receptacle 115 and ceramic longwise member 70 wherein the pilot portion 95 of the longwise member 70 is inserted into the primary void 135 of the receptacle 115 having the slidable contacting interface 200, further shown is the retention gap 190, and the tertiary void 180 with the cantilever configuration 85 of the distal end portion 80 of the longwise member 70, along with an adhesive 210 that is disposed within the open gap 205 volume and the tertiary void 180.

Figure 5:
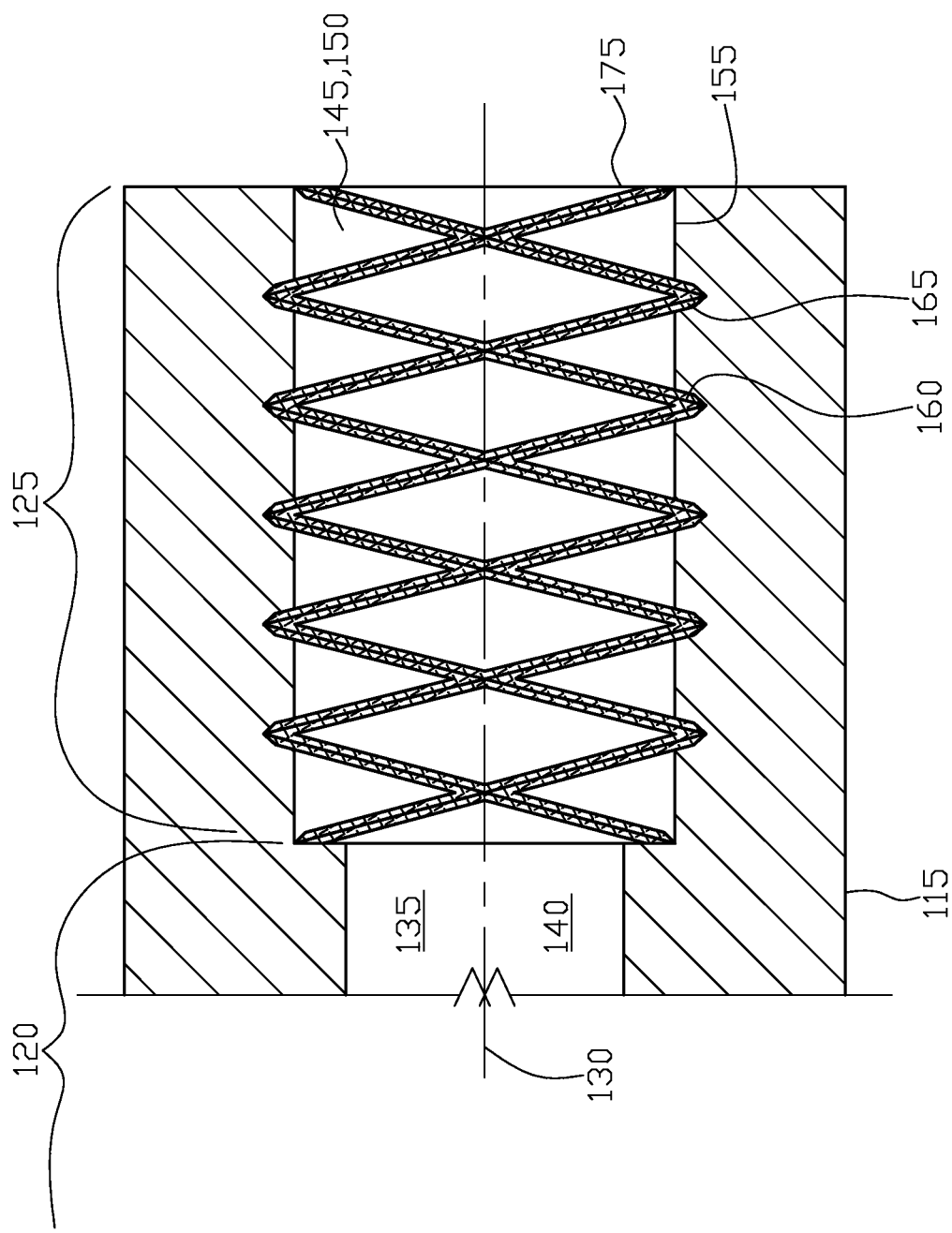
FIG. 5 shows a cross section view of the receptacle secondary void with an inner secondary surface that has a female right hand thread helix groove and a female left hand thread helix groove.
Figure 6:
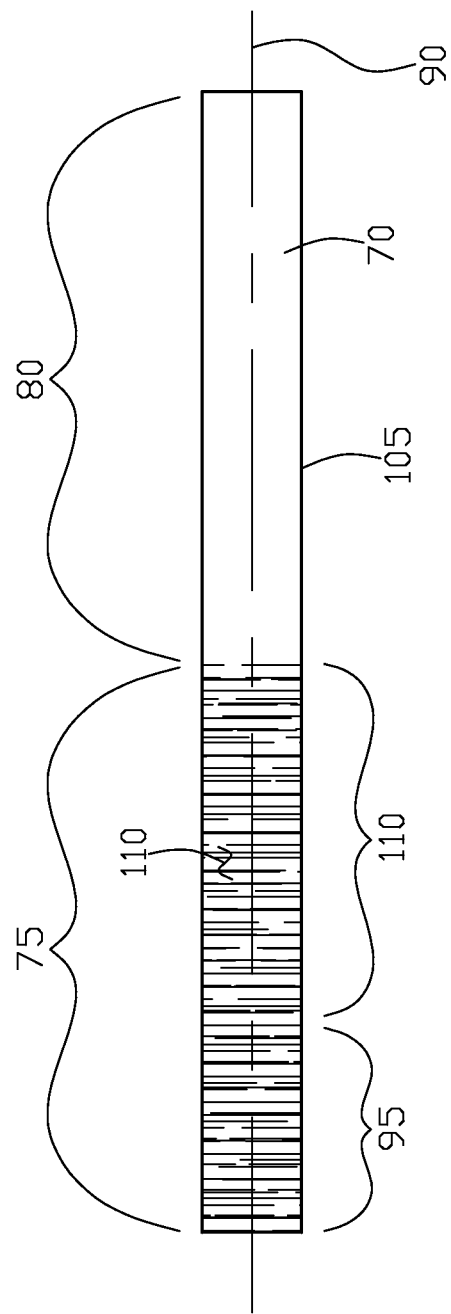
FIG. 6 shows a side elevation view of the ceramic longwise member wherein an outer surface is ground on a proximal end portion of the longwise member.
Figure 7:
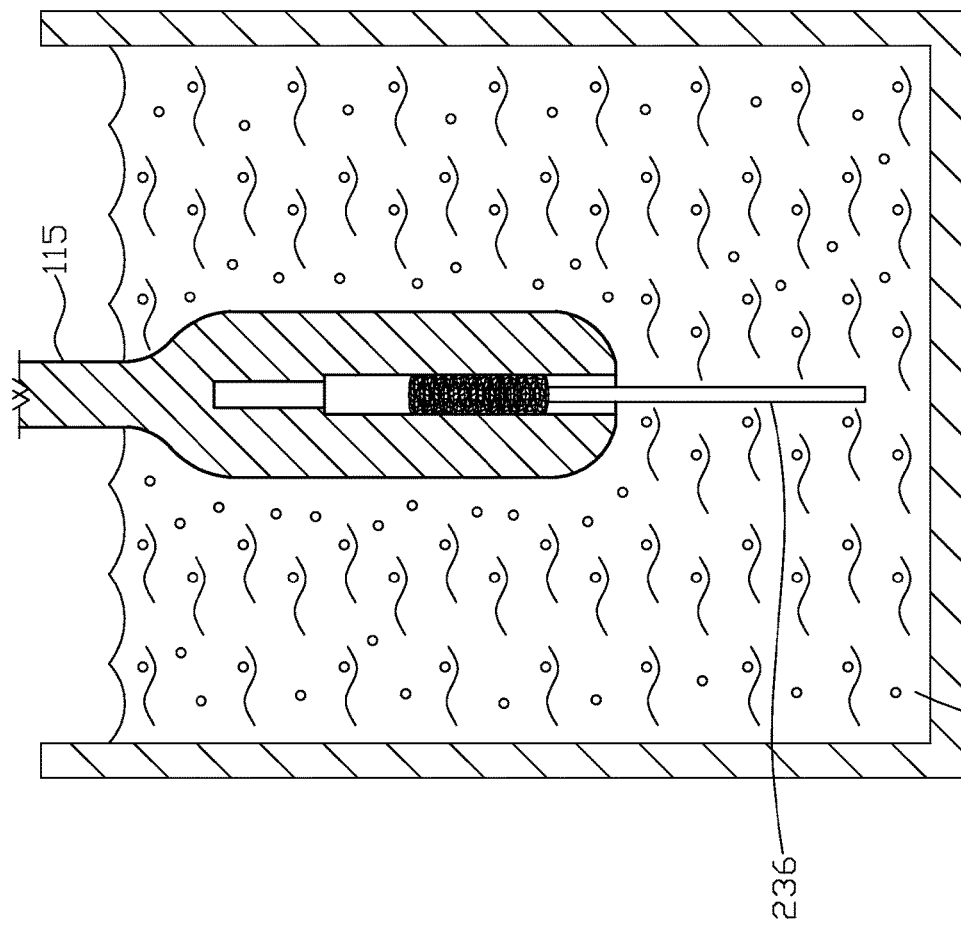
FIG. 7 shows an immersion bath cleaning setup for the receptacle being in particular the primary void, the secondary void, and could also be the tertiary void, further a cleaning brush is shown.

Moving onward, FIG. 5 shows a cross section view of the receptacle secondary void 145 with an inner secondary surface 155 that has a female right hand thread helix groove 160 and a female left hand thread helix groove 165. Continuing, FIG. 6 shows a side elevation view of the ceramic longwise member 70 wherein an outer surface 105 is ground 110 on a proximal end portion 75 of the longwise member 70. Further, FIG. 7 shows an immersion bath 225, 230, 240, 245, 250, 255, 260, 270 cleaning setup for the receptacle 115 being in particular the primary void 135, the secondary void 145, and could also be for the tertiary void 180; further a cleaning brush 235 is shown.

Figure 8:
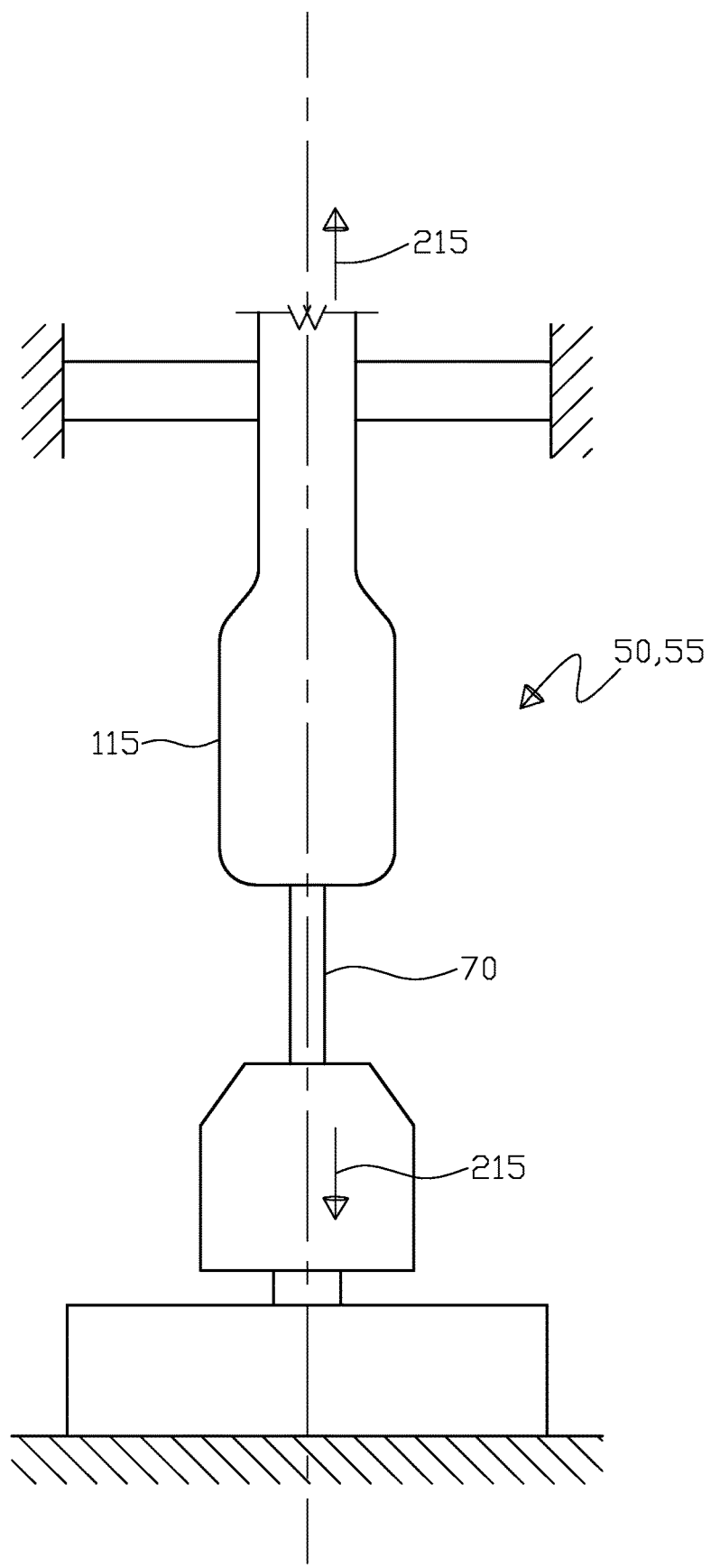
FIG. 8 shows the tensile test setup for the apparatus that includes the receptacle and the longwise member, that are affixed to one another via the adhesive, with force applied to failure test the pull out strength of the longwise member that is affixed to the receptacle axially along the longwise and longitudinal axes.
Figure 9:
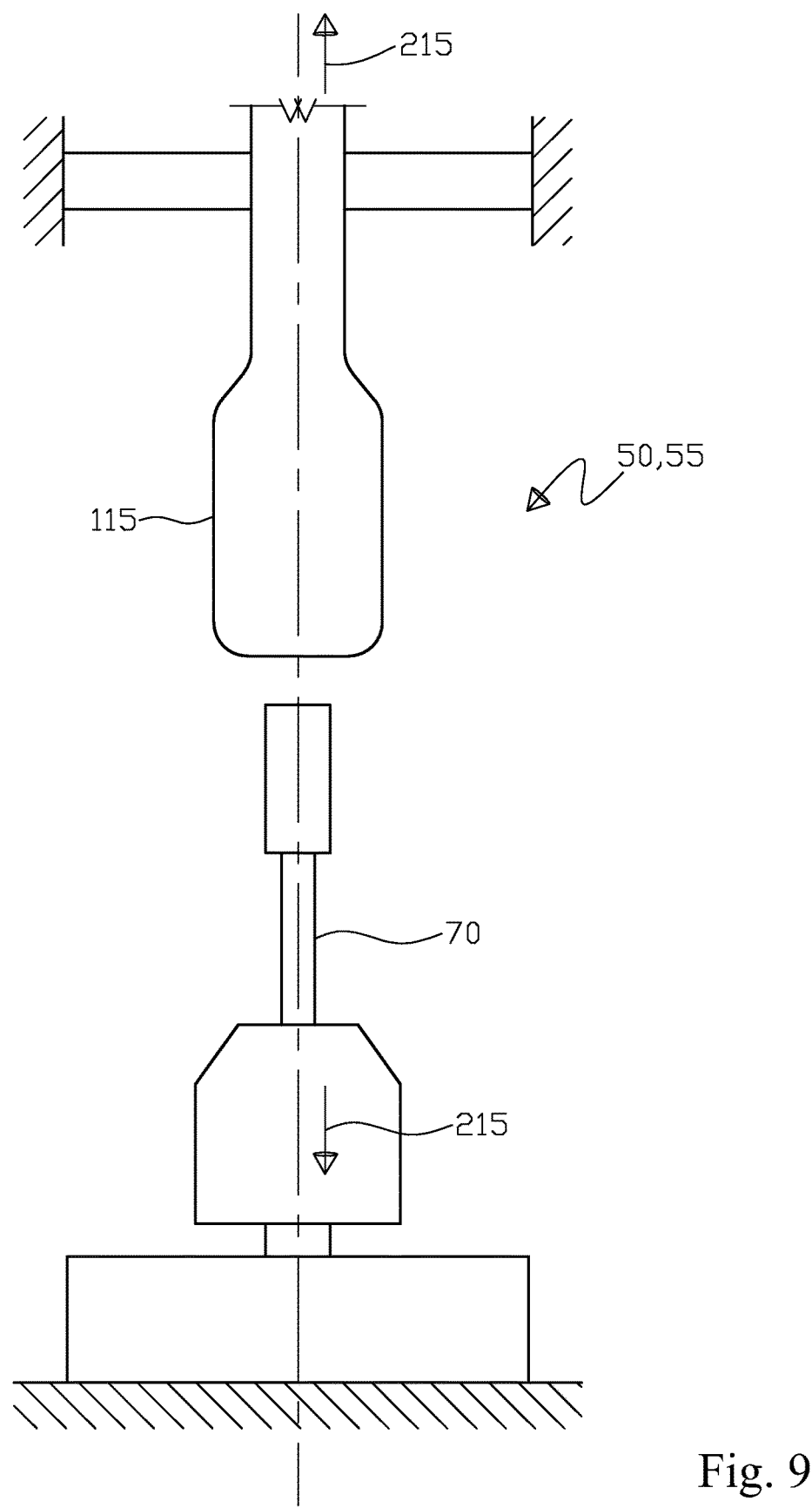
FIG. 9 shows the tensile test setup as described in FIG. 8, for the apparatus after pullout failure showing that the adhesive failed in shear as against the inner secondary surface, wherein the adhesive retained bonding contact with the longwise member.
Figure 10:
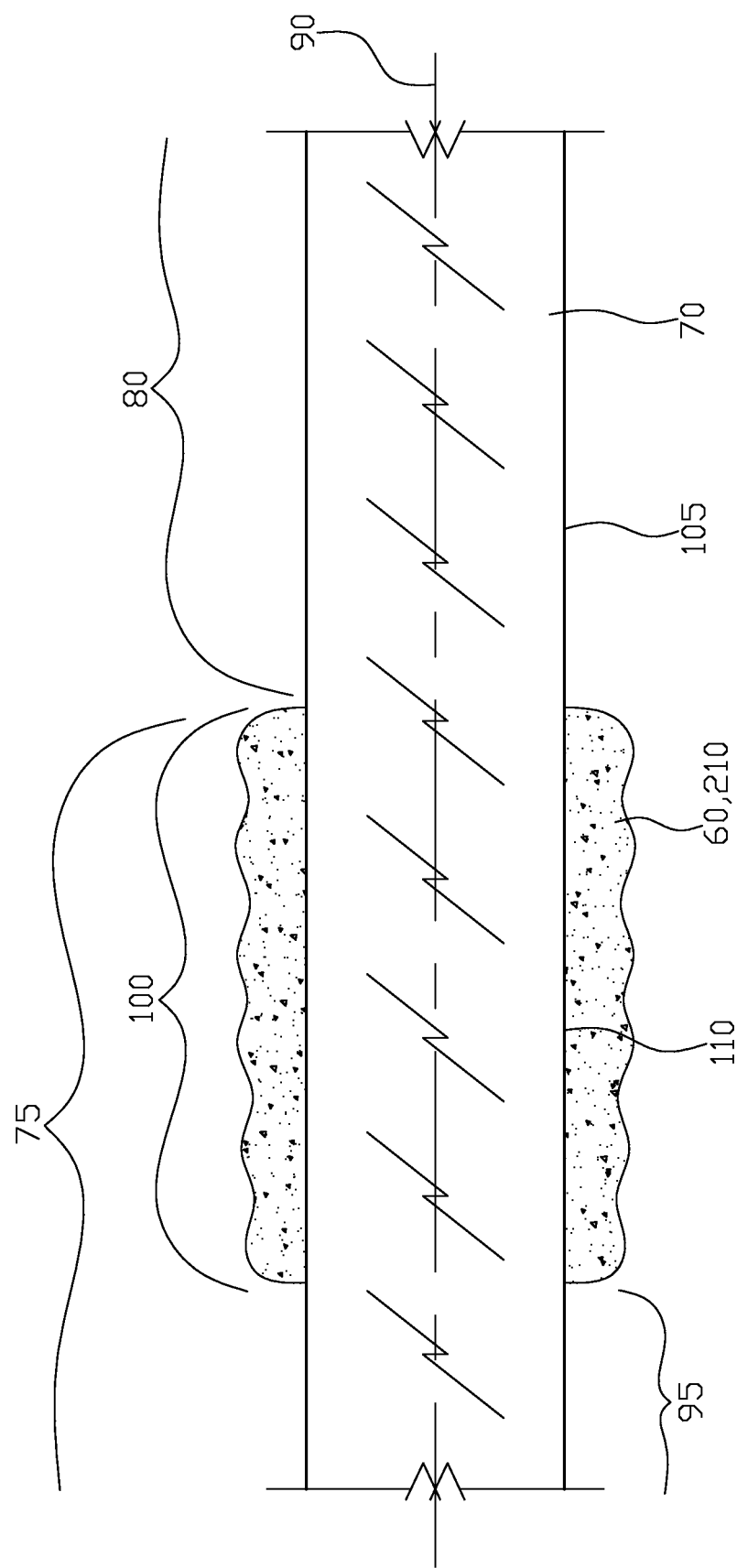
FIG. 10 shows an expanded side elevation view of the longwise member after failure from separating from the receptacle FIG. 9, wherein the adhesive retained bonding contact with the longwise member and the adhesive failed in shear as against the inner secondary surface.

Continuing, FIG. 8 shows the tensile test setup for the apparatus 55 that includes the receptacle 115, the longwise member 70, that are both affixed 50 to one another via the adhesive 210, with force 215 applied to failure test the pull out strength of the longwise member 70 that is affixed 50 to the receptacle 115 axially along the longwise 90 and longitudinal 130 axes. Next, FIG. 9 shows the tensile test setup as described in FIG. 8, for the apparatus 55 after pullout failure showing that the adhesive 210 failed in shear as against the inner secondary surface 155, wherein the adhesive 210 retained bonding contact with the longwise member 70. Further, FIG. 10 shows an expanded side elevation view of the longwise member 70 after failure from separating from the receptacle 115 as shown in FIG. 9, wherein the adhesive 210 retained bonding contact with the longwise member 70 and the adhesive 210 failed in shear as against the inner secondary surface 155.

Broadly, the present invention 50 provides an apparatus 55 and composition 60 for affixment of dissimilar materials, wherein the apparatus 55 and composition 60 include the ceramic longwise member 70 having a proximal end portion 75 and an opposing distal end portion 80 with a longwise axis 90 spanning therebetween. The proximal end portion 75 further having a pilot portion 95 and a suspended portion 100, with the longwise member 70 having an outer surface 105, as shown in FIG. 1. Also included in the apparatus 55 and composition 60 is a steel receptacle 115 including a first end portion 120 and an opposing second end portion 125 with a longitudinal axis 130 spanning therebetween, again see FIG. 1. The first end portion 120 having a primary void 135 that is about the longitudinal axis 130 and the second end portion 125 having a secondary void 145 that is about the longitudinal axis 130, wherein the primary 135 and secondary 145 voids are co-axial to one another, plus further the primary 135 and secondary 145 voids are in communication with one another, also as best shown in FIG. 1.

The primary void 135 defining a primary interior 140 and the secondary void 145 defining a secondary interior 150, with the secondary void 145 terminating in an aperture 175 that is oppositely positioned from the primary void 135, wherein the longwise member 70 proximal end portion 75 is received within the primary 135 and secondary 145 voids wherein the longwise axis 90 and the longitudinal axis 130 are co-axial, also shown in FIG. 1. Also the primary void 135 has a slidable contacting interface 200 with the pilot portion 95 of the longwise member 70 outer surface 105, wherein the primary interior 140 is consumed by the pilot portion 95 of the longwise member 70, and the secondary void 145 forms an open gap volume 205 about the suspended portion 100 of the longwise member 70 outer surface 105. Wherein the secondary interior 150 is further defined by the open gap volume 205 plus the suspended portion 100 of the longwise member 70, wherein the distal end portion 80 of the longwise member 70 projects beyond the aperture 175 in a cantilever configuration 85, see again FIG. 1.

Further included in the apparatus 55 is the composition 60 of an adhesive 210 disposed within the open gap volume 205 that is operational to affix the secondary void 145 to the suspended portion 100 of the longwise member 70 outer surface 105 resulting in the longwise member 70 and the receptacle 115 resisting a separating force 215 along the longwise 90 and the longitudinal 130 axes, as best shown in FIG. 3.

Further as an option in referring to FIGS. 2 and 4 in particular, the second end portion 125 also can have a tertiary void 180, wherein the primary 135, secondary 145, and tertiary voids 180 are co-axial to one another, further the primary 135, secondary 145, and tertiary 180 voids are in communication with one another with the tertiary void 180 defining a tertiary interior 185. Wherein the tertiary interior 185 forms a retention gap volume 190 that is adjacent to the secondary interior 150, the retention gap volume 190 is disposed between the primary interior 140 and the aperture 175 such that the tertiary interior 185 extends a greater distance 195 from the longitudinal axis 130 than the aperture 175. Wherein the adhesive 210 is disposed within the open gap volume 205 and the tertiary interior 185, see FIG. 4, that is operational to affix the suspended portion 100 of the longwise member 70 outer surface 105 to the receptacle 115 without the adhesive 210 having to bond to the secondary interior 150 and the tertiary interior 185, resulting in the longwise member 70 and the receptacle 115 resisting a separating force 215 along the longwise 90 and the longitudinal 130 axes.

Another alternative for the apparatus 55 and composition 60 for affixment of dissimilar materials is wherein the outer surface 105 of the proximal end portion 75 of the longwise member 70 is ground 110 to increase a surface area of the outer surface 105 of the proximal end portion 75 for enhanced bonding of the adhesive 210 to the outer surface 105, as best shown in FIG. 6.

A further alternative for the apparatus 55 and composition 60 for affixment of dissimilar materials is wherein the secondary void 145 secondary interior 150 has an inner secondary surface 155 that is grooved with a female right hand thread helix 160 and a female left hand thread helix 165. Wherein operationally, the right 160 and left 165 hand threads further retain the adhesive 210 via the adhesive flowing into the right 160 and left 165 hand threads in the open gap volume 205 both as against axial force 215 along the longwise 90 and longitudinal 130 axes and rotational force 220 that is about the longwise 90 and longitudinal 130 axes, as shown particularly in FIG. 5, plus FIGS. 3 and 4.

In addition, as an option for the apparatus 55 and composition 60 for affixment of dissimilar materials is wherein the secondary void 145 secondary interior 150 has an inner secondary surface 155 that is surface finished 170 with a range of about one hundred fifty to two hundred fifty root mean squared micro-inches thus increasing the effective inner secondary surface 155 area, to further retain the adhesive 210 in the open gap volume 205 both as against axial force 215 along the longwise 90 and longitudinal 130 axes and rotational force 220 that is about the longwise 90 and longitudinal 130 axes, as best shown in FIGS. 3 and 4.

In referring to FIGS. 8-10, a setup of failure axial pull testing is shown, looking at particular at FIGS. 8 and 9, the receptacle 115 is seen as being fixed in place wherein the longwise member 70 is gripped in a collet with axial force 215 applied to try to pull out the longwise member 70 from the receptacle 115 to test the bond on the adhesive 210, thus determining a better performing (higher separating axial force 215) combination of physical structure of the receptacle 115, adhesive type 210, cleaning procedure, and structure of the longwise member 70. This resulted in the previously described configurations of the primary 140, secondary 150, and tertiary 185 interiors, along with the disclosed cleaning procedure 225, 230, 235, 240, 245, 250, 255, 260, and 265, in conjunction with the previously described grinding 110 of the proximal end portion 75 of the ceramic longwise member 70.

Note that in particular as shown in FIG. 10, that the failure as shown in FIG. 9 of the longwise member 70 pulling out of the receptacle 115 due to force 215, that the adhesive 210 exhibited a stronger bond to the outer surface 105 of the longwise member than to the inner secondary surface 155 of the receptacle 115, in other words as FIG. 10 shows the adhesive 210 stayed on the longwise member 70 and separated from the receptacle 115. Thus, to prevent complete separation of the longwise member 70 and the receptacle 115 with the application of force 215 with failure of the adhesive 210 bond to the inner secondary surface 155, the tertiary interior 185 was devised to keep the longwise member 70 within the receptacle 115 upon the aforementioned failure via the use of the tertiary void 180 and interior 185. Also note that the test setup in FIGS. 8 and 9 utilized the receptacle 115 as shown in FIGS. 1 and 3 without the tertiary void 180 and interior 185.

The ceramic longwise member 70 is preferably constructed of a synthetic sapphire about one to three millimeters in cross section, the synthetic sapphire being an anisotropic, rhombohedral structure of the crystalline form of aluminum oxide ($Al_2O_3$). It occurs naturally but is also able to be synthetically created on an industrial scale. It has a high degree of transmission within the ultraviolet and visible light spectrum while possessing a high degree of strength and toughness as well as chemical resistance. Sapphire is able to transmit wavelengths between two hundred (200) nm to seven hundred sixty (760) nm, and even up to five (5) µm without significant distortion. It also has a compressive strength of 20,000 $kg/cm^2$, with a tensile strength of 7,000 $kg/cm^2$, and a fracture toughness in the range of 2.4-4.5 MPA√M (Pascals per square root meters). Sapphire also has a high abrasion resistance so it will not easily scratch which could cause distortion or reflection of wavelengths.

Wherein a preferred radial clearance of about one-thousandth of an inch is at the pilot 95 and primary interior 140 interface forming the slidable contacting interface 200 and a preferred radial clearance of about five-thousandths of an inch as between the inner secondary surface 155 and the suspended portion 100 thus forming the open gap 205, see in particular FIGS. 1 to 4. The preferred adhesive 210 is LOCTITE #M31CL medical grade epoxy with ISO certification 10993, or MASTERBOND EP42HT-2MED, 2-part epoxy systems, or AXIS 962, being a UV cured adhesive with ISO certification 10993, class VI for medical use, or a suitable equivalent. The preferred construction material of the receptacle 115 is stainless steel.

Method of Manufacture

Referring to FIGS. 1 to 4, and 7, a method 65 for manufacturing an apparatus 55 and composition 60 for affixment of dissimilar materials is disclosed, wherein the method 65 for manufacturing includes the steps of initially providing the apparatus 55 and composition 60 as previously described including the ceramic longwise member 70, the steel receptacle 115, and the adhesive 210.

A next step of cleaning the primary 140, secondary 150, and tertiary 185 interiors for enhanced bonding of the adhesive 210 comprises the following steps of, in referring in particular to FIG. 7;

Firstly, cleaning using soap, hot water, and the scrub brush 235, secondly ultrasonically cleaning with an alkaline solution, thirdly ultrasonically cleaning with an acidic solution, fourthly cleaning by flushing with de-ionized water, fifthly cleaning by flushing with alcohol, sixthly cleaning by flushing with acetone, and seventh cleaning by passivating 265 with heat.

Concerning the ceramic longwise member 70 a further step of grinding 110 the outer surface 105 of the proximal end portion 75 of the longwise member 70 to increase the surface area of the outer surface 105 of the proximal end portion 75 for enhanced bonding of the adhesive 210.

Next a subsequent step of inserting 270 the longwise member 70 into the receptacle 115 such that the proximal end portion 75 pilot portion 95 is inserted 270 into the primary interior 140, see in particular FIG. 2.

Further, referring in particular to FIG. 4, a subsequent step of disposing the adhesive 210 within the open gap volume 205 and the tertiary interior 185 that is operational to affix the suspended portion 100 of the longwise member 70 outer surface 105 to the receptacle 115 via the adhesive 210 bonding to the secondary interior 150 and the tertiary interior 185. Wherein the tertiary interior 185 further retains the adhesive 210 within the receptacle 115 resulting in the longwise member 70 and the receptacle 115 resisting a separating force 215 along the longwise 90 and the longitudinal 130 axes.

As an added step for the method 65 for manufacturing the apparatus 55 and composition 60 for affixment of dissimilar materials in wherein the longwise member 70 is transparent and the adhesive 210 is ultraviolet light curable, a step of applying an ultraviolet light 275 to the distal end portion 80 to cure 280 the adhesive 210 subsequent to the step of disposing the adhesive 210 within the open gap volume 205 and the tertiary interior 185.

CONCLUSION

Accordingly, the present invention of a dissimilar material affixment apparatus, composition, and method has been described with some degree of particularity directed to the embodiment(s) of the present invention. It should be appreciated, though; that the present invention is defined by the following claims construed in light of the prior art so modifications or changes may be made to the exemplary embodiment(s) of the present invention without departing from the inventive concepts contained therein.

The invention claimed is:
1. An apparatus and composition for affixment of dissimilar materials, said apparatus and composition comprising:

(a) a ceramic longwise member including a proximal end portion and an opposing distal end portion with a longwise axis spanning therebetween, said proximal end portion further having a pilot portion and a suspended portion, said longwise member having an outer surface;

(b) a steel receptacle including a first end portion and an opposing second end portion with a longitudinal axis spanning therebetween, said first end portion having a primary void that is about said longitudinal axis and said second end portion having a secondary void that is about said longitudinal axis, wherein said primary and secondary voids are co-axial to one another, further said primary and secondary voids are in communication with one another, said primary void defining a primary interior and said secondary void defining a secondary interior, with said secondary void terminating in an aperture that is oppositely positioned from said primary void, said longwise member proximal end portion is received within said primary and secondary voids wherein said longwise axis and said longitudinal axis are co-axial, wherein said primary void has a slidable contacting interface with said pilot portion of said longwise member outer surface, wherein said primary interior is consumed by said pilot portion of said longwise member, and said secondary void forms an open gap volume about said suspended portion of said longwise member outer surface, wherein said secondary interior is further defined by said open gap volume plus said suspended portion of said longwise member, wherein said distal end portion of said longwise member projects beyond said aperture in a cantilever configuration; and (c) an adhesive disposed within said open gap volume that is operational to affix said secondary void to said suspended portion of said longwise member resulting in said longwise member and said receptacle resisting a separating force along said longwise and said longitudinal axes.

2. An apparatus and composition for affixment of dissimilar materials according to claim 1 wherein said outer surface of said longwise member is ground to increase a surface area of said outer surface for enhanced bonding of said adhesive.

3. An apparatus and composition for affixment of dissimilar materials according to claim 2 wherein said secondary interior has an inner secondary surface that is grooved with a female right hand thread helix and a female left hand thread helix, wherein operationally said right and left hand threads further retain said adhesive in said open gap volume both as against axial force along said longwise and longitudinal axes and rotational force that is about said longwise and longitudinal axes.

4. An apparatus and composition for affixment of dissimilar materials according to claim 2 wherein said secondary interior has an inner secondary surface that is finished with a range of about one hundred fifty to two hundred fifty root mean squared micro-inches, to further retain said adhesive in said open gap volume both as against axial force along said longwise and longitudinal axes and rotational force that is about said longwise and longitudinal axes.

5. An apparatus and composition for affixment of dissimilar materials, said apparatus and composition comprising:

(a) a ceramic longwise member including a proximal end portion and an opposing distal end portion with a longwise axis spanning therebetween, said proximal end portion further having a pilot portion and a suspended portion, said longwise member having an outer surface;

(b) a steel receptacle including a first end portion and an opposing second end portion with a longitudinal axis spanning therebetween, said first end portion having a primary void that is about said longitudinal axis and said second end portion having a secondary void that is about said longitudinal axis, said second end portion also having a tertiary void, wherein said primary, secondary, and tertiary voids are co-axial to one another, further said primary, secondary, and tertiary voids are in communication with one another, said primary void defining a primary interior, said secondary void defining a secondary interior, and said tertiary void defining a tertiary interior, with said secondary void terminating in an aperture that is oppositely positioned from said primary void, said longwise member proximal end portion is received within said primary and secondary voids wherein said longwise axis and said longitudinal axis are co-axial, wherein said primary void has a slidable contacting interface with said pilot portion of said longwise member outer surface, wherein said primary interior is consumed by said pilot portion of said longwise member, and said secondary void forms an open gap volume about said suspended portion of said longwise member outer surface, wherein said secondary interior is further defined by said open gap volume plus said suspended portion of said longwise member, wherein said tertiary interior forms a retention gap volume that is adjacent to said secondary interior, said retention gap volume is disposed between said primary interior and said aperture such that said tertiary interior extends a greater distance from said longitudinal axis than said aperture, wherein said distal end portion of said longwise member projects beyond said aperture in a cantilever configuration; and (c) an adhesive disposed within said open gap volume and said tertiary interior that is operational to affix said suspended portion of said longwise member to said receptacle without said adhesive bonding to said secondary interior and said tertiary interior, resulting in said longwise member and said receptacle resisting a separating force along said longwise and said longitudinal axes.

6. An apparatus and composition for affixment of dissimilar materials according to claim 5 wherein said outer surface of said longwise member is ground to increase a surface area of said outer surface for enhanced bonding of said adhesive.

7. An apparatus and composition for affixment of dissimilar materials according to claim 6 wherein said secondary interior has an inner secondary surface that is grooved with a female right hand thread helix and a female left hand thread helix, wherein operationally said right and left hand threads further retain said adhesive in said open gap volume both as against axial force along said longwise and longitudinal axes and rotational force that is about said longwise and longitudinal axes.

8. An apparatus and composition for affixment of dissimilar materials according to claim 6 wherein said secondary interior has an inner secondary surface that is finished with a range of about one hundred fifty to two hundred fifty root mean squared micro-inches, to further retain said adhesive in said open gap volume both as against axial force along said longwise and longitudinal axes and rotational force that is about said longwise and longitudinal axes.

9. A method for manufacturing an apparatus and composition for affixment of dissimilar materials, said method for manufacturing comprising the steps of:

(a) providing a ceramic longwise member including a proximal end portion and an opposing distal end portion with a longwise axis spanning therebetween, said proximal end portion further having a pilot portion and a suspended portion, said longwise member having an outer surface;

(b) providing a steel receptacle including a first end portion and an opposing second end portion with a longitudinal axis spanning therebetween, said first end portion having a primary void that is about said longitudinal axis and said second end portion having a secondary void that is about said longitudinal axis, said second end portion also having a tertiary void, wherein said primary, secondary, and tertiary voids are co-axial to one another, further said primary, secondary, and tertiary voids are in communication with one another, said primary void defining a primary interior, said secondary void defining a secondary interior, and said tertiary void defining a tertiary interior, with said secondary void terminating in an aperture that is oppositely positioned from said primary void, said longwise member proximal end portion is received within said primary and secondary voids wherein said longwise axis and said longitudinal axis are co-axial, wherein said primary void has a slidable contacting interface with said pilot portion of said longwise member outer surface, wherein said primary interior is consumed by said pilot portion of said longwise member, and said secondary void forms an open gap volume about said suspended portion of said longwise member outer surface, wherein said secondary interior is further defined by said open gap volume plus said suspended portion of said longwise member, wherein said tertiary interior forms a retention gap volume that is adjacent to said secondary interior, said retention gap volume is disposed between said primary interior and said aperture such that said tertiary interior extends a greater distance from said longitudinal axis than said aperture, wherein said distal end portion of said longwise member projects beyond said aperture in a cantilever configuration;

(c) providing an adhesive;

(d) cleaning said primary, secondary, and tertiary interiors for enhanced bonding of said adhesive, via;
  (d)(i) using soap, hot water, and brush;
  (d)(ii) ultrasonically with an alkaline solution;
  (d)(iii) ultrasonically with an acidic solution;
  (d)(iv) flushing with de-ionized water;
  (d)(v) flushing with alcohol;
  (d)(vi) flushing with acetone;
  (d)(vii) passivating with heat;

(e) grinding said outer surface of said longwise member to increase a surface area of said outer surface for enhanced bonding of said adhesive;

(f) inserting said longwise member into said receptacle such that said proximal end portion pilot portion is inserted into said primary interior; and (g) disposing said adhesive within said open gap volume and said tertiary interior that is operational to affix said suspended portion of said longwise member to said receptacle via said adhesive bonding to said secondary interior and said tertiary interior, wherein said tertiary interior further retains said adhesive within said receptacle resulting in said longwise member and said receptacle resisting a separating force along said longwise and said longitudinal axes.

10. A method for manufacturing an apparatus and composition for affixment of dissimilar materials according to claim 9 wherein said longwise member is transparent and said adhesive is ultraviolet light curable, further comprising a step of applying an ultraviolet light to said distal end portion to cure said adhesive subsequent to said step (g).

* * * * *